(12) United States Patent
Feng et al.

(10) Patent No.: US 12,196,723 B2
(45) Date of Patent: Jan. 14, 2025

(54) LARGE-SCALE THREE-DIMENSIONAL PHYSICAL SIMULATION TEST SYSTEM FOR WHOLE DEVELOPMENT PROCESS OF DEEP ENGINEERING ROCK BURST

(71) Applicant: Northeastern University, Shenyang (CN)

(72) Inventors: Xiating Feng, Shenyang (CN); Xiwei Zhang, Shenyang (CN); Lei Shi, Shenyang (CN); Zhibin Yao, Shenyang (CN)

(73) Assignee: NORTHEASTERN UNIVERSITY, Shenyang (CN)

( * ) Notice: Subject to any disclaimer, the term of this patent is extended or adjusted under 35 U.S.C. 154(b) by 0 days.

(21) Appl. No.: 17/912,926

(22) PCT Filed: Jul. 22, 2022

(86) PCT No.: PCT/CN2022/107219
§ 371 (c)(1),
(2) Date: Sep. 20, 2022

(87) PCT Pub. No.: WO2024/011651
PCT Pub. Date: Jan. 18, 2024

(65) Prior Publication Data
US 2024/0230495 A1 Jul. 11, 2024

(30) Foreign Application Priority Data
Jul. 13, 2022 (CN) .......................... 202210820592.6

(51) Int. Cl.
*G01N 3/30* (2006.01)
*G01N 3/10* (2006.01)
*G01N 33/24* (2006.01)

(52) U.S. Cl.
CPC ................. *G01N 3/30* (2013.01); *G01N 3/10* (2013.01); *G01N 33/24* (2013.01);
(Continued)

(58) Field of Classification Search
CPC ............... G01N 3/10; G01N 3/24; G01N 3/30
See application file for complete search history.

(56) References Cited

U.S. PATENT DOCUMENTS 9,316,568 B2 * 4/2016 He .......................... G01N 3/068
10,564,080 B2 * 2/2020 Ju ............................ G01N 3/12
(Continued)

FOREIGN PATENT DOCUMENTS

| CN | 101914912 A | 12/2010 |
|---|---|---|
| CN | 103398861 A | 11/2013 |

(Continued)

OTHER PUBLICATIONS

Lang et al., "Research on model test and mechanical mechanism of strain rockbursts", p. 2733-2741, ISSN: 1000-6915, vol. 37, issue No. 12, Dec. 31, 2018, 25 pages.
(Continued)

*Primary Examiner* — Erika J. Villaluna
(74) *Attorney, Agent, or Firm* — MUNCY, GEISSLER, OLDS & LOWE, P.C.

(57) ABSTRACT

The invention relates to a large-scale three-dimensional physical simulation test system for the whole development process of deep engineering rock burst. A $CO_2$ blast cracking device, a dynamic fiber grating and ultrasonic probes are pre-embedded in a physical model sample of similar materials. Acoustic emission probes are pre-mounted on the boundary of a sample. A tunnel excavated in the sample is provided with a three-way acceleration sensor and an industrial endoscope. A sample 3D printer and a drop hammer impact device are arranged outside the three-dimensional
(Continued)

static stress loading device. A hydraulic oil source and a controller are arranged outside the three-dimensional static stress loading device and mounted on the ground. The controller is connected with a computer.

10 Claims, 4 Drawing Sheets

(52) U.S. Cl.
CPC .............. *G01N 2203/001* (2013.01); *G01N 2203/0019* (2013.01); *G01N 2203/0026* (2013.01); *G01N 2203/0044* (2013.01); *G01N 2203/0048* (2013.01); *G01N 2203/0053* (2013.01); *G01N 2203/0067* (2013.01); *G01N 2203/0256* (2013.01); *G01N 2203/0298* (2013.01); *G01N 2203/0605* (2013.01); *G01N 2203/0611* (2013.01); *G01N 2203/0635* (2013.01); *G01N 2203/0641* (2013.01); *G01N 2203/0658* (2013.01)

(56) References Cited

U.S. PATENT DOCUMENTS

| | | | |
|---|---|---|---|
| 11,119,018 B2 * | 9/2021 | Feng | ................... G01N 3/12 |
| 2020/0132577 A1 | 4/2020 | Kwon et al. | |

FOREIGN PATENT DOCUMENTS

| | | |
|---|---|---|
| CN | 106840892 A | 6/2017 |
| CN | 107014690 A | 8/2017 |
| CN | 108519282 A | 9/2018 |
| CN | 108827578 A | 11/2018 |
| CN | 109991148 A | 7/2019 |
| CN | 111006953 A | 4/2020 |
| JP | 2003129458 A | 5/2003 |

OTHER PUBLICATIONS

Hui et al., "Research status and thinking of physical simulation test for rockbursts", p. 915-923, ISSN: 1000-6915, vol. 34, issue No. 5, May 31, 2015, 25 pages.

* cited by examiner

LARGE-SCALE THREE-DIMENSIONAL PHYSICAL SIMULATION TEST SYSTEM FOR WHOLE DEVELOPMENT PROCESS OF DEEP ENGINEERING ROCK BURST

BACKGROUND OF THE INVENTION

1. Field of the Invention

The invention relates to the technical field of rock mechanical test, and particularly relates to a large-scale three-dimensional physical simulation test system for the whole development process of deep engineering rock burst.

2. The Prior Arts

With continuous increase of the burial depth of rock mass engineering, a rock mass is in a true triaxial stress state and the level of in-situ stress is significantly increased. Excavation under such high stress conditions will easily lead to sudden release of elastic potential energy of deformation, accumulated in the rock masses. Then the rock burst phenomenon of violent failure and ejection of surrounding rocks occur, resulting in casualties, delay in construction period, damage to machinery and equipment and other accidents. According to spatiotemporal characteristics of occurrence of the rock burst, the rock burst can be divided into immediate rock burst, time delayed rock burst, intermittent rock burst and chain rock burst. The immediate rock burst refers to the rock burst that occurs during the excavation and unloading process, and usually occurs within a few hours or 1-3 days after the excavation of the rock mass. The time delayed rock burst refers to the rock burst that occurs due to external disturbances after three-dimensional stress adjustment and balance of excavation unloading, which generally occurs several days to several months after excavation. The intermittent rock burst refers to the rock burst of the same level or higher intensity multiple times in the same zone within a certain period of time. The chain rock burst refers to a chain of rock bursts at multiple positions initiated by a first rock burst. Therefore, the spatiotemporal characteristics of the rock burst show that its essence is a geological disaster caused by the micro-fault and subcritical instability of the rock mass after excavation and unloading under the disturbance of dynamic stress waves having different characteristics.

According to an occurrence mechanism of the rock burst, it can be divided into strain bursts, strain-structure slip rock bursts and fault slip rock bursts. The strain bursts mainly occur in intact and hard unstructured plane rock masses, wherein stress plays a leading role. The strain-structural slip rock bursts mainly occur in hard rock masses containing sporadic structural planes or bedding planes. The structural planes control the boundary of blasting pit, and are generally more destructive than the strain rock bursts. The stress and the structural planes in the strain-structural slip rock bursts play a leading role together. The fault slip rock burst mainly occurs in the rock mass with the existence of large-scale fault structure, which has a larger impact are and stronger destructive power, and may even induce strong continuous rock burst. In the fault slip rock burst, the fault structure of the rock mass play a leading role. Therefore, the occurrence mechanism of the rock burst shows that the rock burst is affected by factors such as the nature of the rock mass (occurrence of the structural planes) and the level of the in-situ stress, among which the local high stress environment where the structures are located is an induced coupling factor.

At present, rock mass excavation methods mainly comprise a drilling and blasting method and a TBM construction method, and the rock mass excavation methods are also another important factor affecting the rock burst. The rock-breaking process of the drilling and blasting method is that the dynamic action of shock wave and its generated stress wave is completed together with static pressure action of blasting gas. The stress concentration area of a surrounding rock area caused by excavation is far away from a tunnel wall, and a stress gradient formed is small. The TBM construction method is a construction method using a full-section hard rock tunnel boring machine to excavate the tunnel, the stress concentration area of the surrounding rock caused by excavation is relatively close to the tunnel wall, and the formed stress gradient is larger. Under the same conditions, the probability of the time delayed rock burst in the construction process of the drilling and blasting method is greater than that in the TBM construction method.

At present, the construction process of major rock mass projects mostly relies on on-site in-situ micro seismic monitoring methods to provide early warning of rock burst disasters. Although the construction safety is guaranteed to a certain extent, the in-situ micro seismic monitoring research is mostly a kind of posterior analysis due to weak repeatability of rock bursts at the project site, which hinders further improvement of the evolution reliability of a micro seismic early warning mechanism. Therefore, it is very necessary to carry out an indoor simulation test of rock burst with multiple types and factors. The large-scale three-dimensional physical simulation test device and technology for the whole development process of multi type rock burst in deep engineering can be used to explore and reveal the development mechanism of major disasters of the deep engineering rock burst. A series of technical problems in mechanism deduction, rock burst prediction and prevention and control of multi type rock burst disasters in deep engineering caused by complex and changeable geological conditions, extreme occurrence environment, various engineering activities and other factors are solved.

A large-scale three-dimensional physical model test device is used to load and unload the three-dimensional physical model sample of similar materials of meter size to simulate rock bursts. Although the device has the characteristics of simple operation, controllable incentives, rich and intuitive test results, repeatability, and the like, the existing three-dimensional similar material physical model test mainly simulates immediate rock burst and strain bursts under static stress, and the continuous ejection process of rock blocks cannot be presented in the test process. In addition, the existing large-scale three-dimensional physical model test device cannot realize rock burst simulation under multi-type and multi-influencing factors. The specific reasons are as follows:

(1) High Stress Loading Capacity is Insufficient

The existing large-scale three-dimensional physical model test device mainly adopts a steel plate welding-bolt splicing frame structure, which has structural design defects such as low bearing capacity, large deformation, and weak dynamic loading and vibration resistance, In addition, the splicing frame structure has low rigidity and weak seismic resistance, resulting in the maximum loading capacity of the test device is only 10 MPa, and its stress loading capacity cannot generate sufficient effective concentrated stress in the tunnel inside the model sample. It is even impossible to destroy the three-dimensional physical model sample of similar materials of meter size, resulting in insufficient ejection (projection) kinetic energy of the similar material bodies, and is unable to simulate the continuous ejection phenomenon of the rock blocks similar to engineering rock bursts.

(2) Three-Dimensional Stress Coordination Boundary Loading Technology is not Perfect The three-dimensional stress output by the existing large-scale three-dimensional physical model test device is mainly realized by array-type single-acting jacks. There are many problems such as difficulty in simultaneous loading of multiple single-acting jacks, a large number of empty blank bands loaded on the sample, and uncontrollable stress concentration locally on the sample, resulting in the local stress field in the three-dimensional physical model is inconsistent with the theoretical calculation of elastic mechanics, and the stress concentration position cannot be effectively evaluated.

(3) Multi-Source Dynamic Disturbance Simulation Technology is Insufficient

The frequency of dynamic stress waves generated by the TBM construction method and the drilling and blasting excavation method is from Hz to MHz, the distance from a disturbance source to a tunnel face is from centimetre (cm) to meter (m), and the disturbance frequency may be single or continuous. At present, the existing large-scale three-dimensional physical model test device mainly uses dynamic hydraulic actuators to realize dynamic disturbance of sample ends. However, the existing commercial dynamic hydraulic actuators are mainly low-frequency and high-capacity dynamic hydraulic actuators and high-frequency and low-capacity dynamic hydraulic actuators, which cannot effectively simulate the dynamic amplitude-frequency characteristics of engineering rock bursts in large-scale three-dimensional physical model tests. The three-dimensional physical model sample of similar materials of meter size needs to use the large-tonnage hydraulic actuator, and the dynamic hydraulic actuator needs to consider amplitude-frequency characteristics and power output response. The requirements for the mechanical-hydraulic-control-rock mechanics mutual-feedback design method are high, resulting in the unsolved technical problems of high tonnage and high (acceleration) output of the hydraulic actuator under high frequency conditions. Except that the dynamic hydraulic actuators are used to disturb the end of the sample, the existing large-scale three-dimensional physical model test device does not consider a multi-source disturbance technology, and cannot realize research on the development mechanism of the rock burst induced by multi-source disturbance.

(4) Local High Stress Environment Reconstruction Technology is Insufficient

In the large-scale three-dimensional physical model test, the boundary high stress cannot be completely transferred to a specific structure in the model sample due to the offset of interface friction, and the stress transfer efficiency is not high due to the porosity of the similar materials, so that effective local high stress environment at specific positions in the model sample cannot be realized. First of all, when the stress state of the structural planes of the three-dimensional physical model sample of similar materials enters into subcritical failure, an effective disturbance source or effective stress concentration cannot be generated to induce the failure, which limits the simulation of the strain-structural slip rock bursts and simulates fault slip rock bursts. Secondly, high stress or disturbance stress cannot be transferred to the model tunnel in a state of stress equilibrium, which limits the simulation of time delayed rock burst. Thirdly, the jump migration of the stress field cannot be realized, which limits the simulation of the chain rock bursts.

(5) The Excavation Method is Inconsistent with the Technical Process Currently Used in the Deep Engineering Due to control of explosives, the excavation of indoor large-scale three-dimensional physical model samples can only be carried out by opening holes first and then loading, or the drilling machine can only be used for small-section reaming during the sample loading process, which causes problems that leads to the failure of effectively simulating the whole process of rock breaking by the drilling and blasting method and the TBM construction method in the test process, and thus the process attribute of rock burst disturbed by the excavation cannot be simulated.

SUMMARY OF THE INVENTION

In view of the problems existing in the prior art, the invention provides a large-scale three-dimensional physical simulation test system for the whole development process of deep engineering rock burst, which has high stress loading capability, improves the three-dimensional stress coordination boundary loading technology, proposes multi-source dynamic disturbance simulation technology, proposes local high stress environment reconstruction technology, and proposes TBM construction method and drilling and blasting method excavation simulation technology consistent with a project site, and thus a rock burst information intelligent perception technology is perfected.

In order to realize the above objectives, the present invention adopts the following technical scheme that a large-scale three-dimensional physical simulation test system for the whole development process of deep engineering rock burst comprises a three-dimensional static stress loading device, a 3D printer for a physical model sample of similar materials, a $CO_2$ blast cracking device, a split Hopkinson pressure bar device, a miniature rotary excavation flexible mechanical arm device, a drop hammer impact device, a hydraulic oil source and a controller. The $CO_2$ blast cracking device is arranged in the physical model sample of similar materials, and the physical model sample of similar materials is located in the three-dimensional static stress loading device. The split Hopkinson pressure bar device and the miniature rotary excavation flexible mechanical arm device are arranged outside the three-dimensional static stress loading device, and the split Hopkinson pressure bar device, the three-dimensional static stress loading device and the miniature rotary excavation flexible mechanical arm device are arranged in a linear order and all of them are fixedly mounted on the ground. The 3D printer for a physical model sample of similar materials is located outside the three-dimensional static stress loading device, and is mounted on the ground through a track movement structure, and a moving path of the 3D printer for a physical model sample of similar materials passes through a position right above the three-dimensional static stress loading device. The drop hammer impact device is located outside the three-dimensional static stress loading device and is mounted on the ground through the track movement structure, and a moving path of the drop hammer impact device passes through the position right above the three-dimensional static stress loading device. The hydraulic oil source and the controller are arranged outside the three-dimensional static stress loading device and both are fixedly mounted on the ground, and the controller is connected with a computer.

The three-dimensional static stress loading device comprises a high-rigidity three-dimensional reaction frame, a first dynamic hydraulic actuator, a second dynamic hydraulic actuator, a first flexible bladder hydraulic pillow, a second flexible bladder hydraulic pillow, a third flexible bladder hydraulic pillow, a fourth flexible bladder hydraulic pillow and a fifth flexible bladder hydraulic pillow. The high-rigidity three-dimensional reaction frame adopts an integral structure, and loading holes are respectively formed on the top, the left side and the right side of the high-rigidity three-dimensional reaction frame. A frame top cover is fixedly mounted on the top of the high-rigidity three-dimensional reaction frame, and the first dynamic hydraulic actuator is vertically and fixedly mounted at the center of the frame top cover. The second dynamic hydraulic actuator is horizontally and fixedly mounted on the left side of the high-rigidity three-dimensional reaction frame. A frame side cover is fixedly mounted on the right side of the high-rigidity three-dimensional reaction frame, and a simulation excavation hole is formed in the center of the frame side cover. The first flexible bladder hydraulic pillow is arranged on the lower surface of the frame top cover, and adopts a circular structure. The second flexible bladder hydraulic pillow is arranged at the bottom of the high-rigidity three-dimensional reaction frame. The third flexible bladder hydraulic pillow is arranged on the front side of the high-rigidity three-dimensional reaction frame. The fourth flexible bladder hydraulic pillow is arranged on the rear side of the high-rigidity three-dimensional reaction frame. The fifth flexible bladder hydraulic pillow is arranged on the inner surface of the frame side cover, and adopts a circular structure.

The first flexible bladder hydraulic pillow is connected with the hydraulic oil source through a hydraulic oil path, and a first pressure sensor is arranged on the hydraulic oil path between the first flexible bladder hydraulic pillow and the hydraulic oil source. The second flexible bladder hydraulic pillow is connected with the hydraulic oil source through the hydraulic oil path, and a second pressure sensor is arranged on the hydraulic oil path between the second flexible bladder hydraulic pillow and the hydraulic oil source. The third flexible bladder hydraulic pillow is connected with the hydraulic oil source through the hydraulic oil path, and a third pressure sensor is arranged on the hydraulic oil path between the third flexible bladder hydraulic pillow and the hydraulic oil source. The fourth flexible bladder hydraulic pillow is connected with the hydraulic oil source through the hydraulic oil path, and a fourth pressure sensor is arranged on the hydraulic oil path between the fourth flexible bladder hydraulic pillow and the hydraulic oil source. The fifth flexible bladder hydraulic pillow is connected with the hydraulic oil source through the hydraulic oil path, and a fifth pressure sensor is arranged on the hydraulic oil path between the fifth flexible bladder hydraulic pillow and the hydraulic oil source. Data output ends of the first pressure sensor, the second pressure sensor, the third pressure sensor, the fourth pressure sensor and the fifth pressure sensor are all electrically connected with the controller.

A piston rod of the first dynamic hydraulic actuator adopts a hollow structure, and a first annular load sensor and a first pressure bearing cushion block are sequentially arranged between the piston rod of the first dynamic hydraulic actuator and the physical model sample of similar materials. A first magnetostrictive displacement sensor is arranged between the piston rod of the first dynamic hydraulic actuator and a cylinder cap. A piston rod of the second dynamic hydraulic actuator adopts a hollow structure, and a second annular load sensor and a second pressure bearing cushion block are sequentially arranged between the piston rod of the second dynamic hydraulic actuator and the physical model sample of similar materials. A second magnetostrictive displacement sensor is arranged between the piston rod of the second dynamic hydraulic actuator and its cylinder cap. The first annular load sensor, the first magnetostrictive displacement sensor, the second annular load sensor and the second magnetostrictive displacement sensor are all electrically connected with the controller.

The hydraulic oil path of the first dynamic hydraulic actuator is connected with the hydraulic oil source through a first servo valve block, and first accumulator groups are mounted on the first servo valve block. An electric control end of the first servo valve block is electrically connected with the controller. The hydraulic oil path of the second dynamic hydraulic actuator is connected with the hydraulic oil source through second servo valve blocks, and second accumulator groups are respectively mounted on the second servo valve blocks. Electric control ends of the second servo valve blocks are electrically connected with the controller.

An emission rod of the split Hopkinson pressure bar device sequentially passes through a center hole of the piston rod of the second dynamic hydraulic actuator and a center hole of the second annular load sensor to be opposite to the second pressure bearing cushion block. A mechanical arm of the miniature rotary excavation flexible mechanical arm device sequentially passes through the simulation excavation hole and a center hole of the fifth flexible bladder hydraulic pillow to be opposite to the physical model sample of similar materials. A drop hammer rod of the drop hammer impact device sequentially passes through the center hole of the piston rod of the first dynamic hydraulic actuator and the center hole of the first annular load sensor to be opposite to the first pressure bearing cushion block.

A dynamic fiber grating and ultrasonic probes are respectively pre-embedded in the physical model sample of similar materials, acoustic emission probes are pre-installed on the boundary of the physical model sample of similar materials, and signal output ends of the dynamic fiber grating, the ultrasonic probes and the acoustic emission probes are all electrically connected with the controller, and after excavation of the tunnel is completed in the physical model sample of similar materials, a three-way acceleration sensor and an industrial endoscope are arranged in a tunnel.

When an immediate strain burst simulation test is carried out, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover with the high-rigidity three-dimensional reaction frame, then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;

Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during the printing process, pre-embedding the dynamic fiber grating and the ultrasonic probes at internal set positions of the physical model sample of similar materials, and pre-mounting the acoustic emission probes at set positions at the boundary of the physical model sample of similar materials;

Step IV: performing in-situ normal temperature curing on the printed physical model sample of similar materials, after the curing period is over, detecting whether the flatness, the verticality and the compactness of the physical model sample of similar materials are qualified. If the flatness, the verticality and the compactness are qualified, detecting whether the dynamic fiber grating, the ultrasonic probes and the acoustic emission probes on the boundary pre-embedded in the physical model sample of similar materials work normally or not. If they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in the maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in the intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in the minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and then continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of the surrounding rock of the wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of maximum principal stress through the first dynamic hydraulic actuator to induce immediate strain burst, and during the process of applying the disturbance loads, monitoring internal deformation of the physical model sample of similar materials through the dynamic fiber grating, monitoring the wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the second flexible bladder hydraulic pillow to the target value of the intermediate principal stress, and then unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

When an immediate strain-structural rock burst simulation test is carried out, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover with the high-rigidity three-dimensional reaction frame, and then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;

Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during the printing process, pre-embedding the dynamic fiber grating and the ultrasonic probes at internal set positions in the physical model sample of similar materials, and pre-mounting the acoustic emission probes at set positions on the boundary of the physical model sample of similar materials; besides, printing a fault structural plane in the physical model sample of similar materials at the same time, wherein the pre-embedded position of the $CO_2$ blast cracking device is near the fault structural plane;

Step IV: performing in-situ normal temperature curing on the printed physical model sample of similar materials, after the curing period is over, detecting whether the flatness, the verticality and the compactness of the physical model sample of similar materials are qualified, if the flatness, the verticality and the compactness are qualified, then detecting whether the dynamic fiber grating, the ultrasonic probes and the acoustic emission probes on the boundary pre-embedded in the physical model sample of similar materials work normally or not, if they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in the maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in the intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in the minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of the surrounding rock of the wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of the maximum principal stress through the first dynamic hydraulic actuator, and at the same time, starting the $CO_2$ blast cracking device to apply burst impact to the physical model sample of similar materials, to induce immediate strain-structural rock burst, and during the process of applying the disturbance loads and the burst impact, monitoring internal deformation of the physical model sample of similar materials through the dynamic fiber grating, monitoring the wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the second flexible bladder hydraulic pillow to the target value of the intermediate principal stress, and then unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

When carrying out time delayed rock burst simulation test, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover with the high-rigidity three-dimensional reaction frame, then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;

Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during the printing process, pre-embedding the dynamic fiber grating and the ultrasonic probes at internal set positions in the physical model sample of similar materials, and pre-mounting the acoustic emission probes at set positions on the boundary of the physical model sample of similar materials;

Step IV: performing in-situ normal temperature curing on the printed physical model sample of similar materials, after the curing period is over, detecting whether the flatness, the verticality and the compactness of the physical model sample of similar materials are qualified, if the flatness, the verticality and the compactness are qualified, detecting whether the dynamic fiber grating, the ultrasonic probes and the acoustic emission probes on the boundary, pre-embedded in the physical model sample of similar materials work normally or not, if they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in the maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in the intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in the minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and then continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of the surrounding rock of the wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of the maximum principal stress through the first dynamic hydraulic actuator to induce low-intensity time delayed rock burst, and then starting the drop hammer impact device, so that the drop hammer rod of the drop hammer impact device freely drops down and impacts the first pressure bearing cushion block, and application of external disturbances is finished to induce middle-intensity time delayed rock burst, and finally, starting the split Hopkinson pressure bar device, so that the emission rod of the split Hopkinson pressure bar device impacts the second pressure bearing cushion block to complete further application of the external disturbances in order to induce high-intensity time delayed rock burst, and during the process of applying the disturbance loads, monitoring internal deformation of the physical model sample of similar materials through the dynamic fiber grating, monitoring the wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the second flexible bladder hydraulic pillow to the target value of the intermediate principal stress, and then unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

The beneficial effects of the present invention are:

(1) Having High Stress Loading Capacity

The three-dimensional static stress loading device of the invention adopts an integrated high-rigidity three-dimensional reaction frame, and the maximum loading capacity can reach 15 MPa, which can generate effective concentrated stress of sufficient magnitude at the excavation of the tunnel in the model sample, and can efficiently adapt to strong dynamic disturbance loading, so that sufficient ejection (projection) of kinetic energy of the similar material bodies can be guaranteed, and the continuous ejection phenomenon of rock blocks similar to rock bursts in engineering sites can be effectively simulated.

(2) Perfecting the Three-Dimensional Stress Coordination Boundary Loading Technology The three-dimensional static stress loading device of the present invention adopts a combined loading structure of the dynamic hydraulic actuator and the flexible bladder hydraulic pillow, which makes synchronous loading easier, eliminates the loading blank band, avoids uncontrollable stress concentration locally on the sample, ensures consistency of the local stress field in the three-dimensional physical model sample and the elastic mechanics theory calculation, and can form effective stress concentration at the tunnel of the model sample.

(3) Providing Multi-Source Dynamic Disturbance Simulation Technology

According to the invention, boundary disturbance of the sample can be realized through the dynamic hydraulic actuator, the burst impact disturbance in the sample can be realized through the $CO_2$ blast cracking device, and external impact disturbance of the sample can be realized through the drop hammer impact device and the split Hopkinson pressure bar device, and thus research on the rock burst mechanism induced by multi-source disturbance can be realized.

(4) Providing Local High Stress Environment Reconstruction Technology

According to the invention, through cooperation of the first dynamic hydraulic actuator and the first flexible bladder hydraulic pillow, and at the same time, through matching a preset fault angle in the sample through the pressure bearing cushion blocks with different inclination angles, a high tangential stress area can be formed at faults (structural planes) or local parts of the tunnel. When the load of the second dynamic hydraulic actuator is reduced alone, a low normal stress area or a low effective stress area can be formed at the faults (structural planes) of the sample or the corresponding orientation of the tunnel; and when partial blasting is carried out in the sample by the $CO_2$ blast cracking device, a partitioned crack zone can be formed in the sample.

(5) Providing an Excavation Simulation Technology of the TBM Construction Method and Drilling and Blasting Method, Consistent with the Engineering Site According to the invention, the TBM excavation process of rock mass engineering can be simulated through the miniature rotary excavation flexible mechanical arm device, and the excavation process of the drilling and blasting method can be simulated through the $CO_2$ blast cracking device, so that the problem of simulating the process attributes of rock burst disturbed by excavation is solved.

(6) Perfecting Rock Burst Information Intelligent Perception Technology

According to the invention, stress information of the sample is monitored through a load sensor and a pressure sensor, the boundary and internal deformation of the sample are monitored through the magnetostrictive displacement sensor and the dynamic fiber grating, ultrasonic information in the sample is monitored through the ultrasonic probes, acoustic emission information at different positions of the sample is monitored through the acoustic emission probes, acceleration information of the elastic wave of the sample during rock burst is monitored through the three-way acceleration sensor, and damage information of the tunnel of the model sample is monitored through the industrial endoscope, so that multi-dimensional intelligent perception of the rock burst information is realized, and thus a technical support is provided for analyzing the rock burst development process and mechanism.

In drawings, 1: three-dimensional static stress loading device; 2: 3D printer for a physical model sample of similar materials; 3: $CO_2$ blast cracking device; 4: split Hopkinson pressure bar device; 5: miniature rotary excavation flexible mechanical arm device; 6: drop hammer impact device; 7: hydraulic oil source; 8: controller; 9: physical model sample of similar materials; 10: high-rigidity three-dimensional reaction frame; 11: first dynamic hydraulic actuator; 12: second dynamic hydraulic actuator; 13: first flexible bladder hydraulic pillow; 14: second flexible bladder hydraulic pillow; 15: third flexible bladder hydraulic pillow; 16: fourth flexible bladder hydraulic pillow; 17: fifth flexible bladder hydraulic pillow; 18: frame top cover; 19: frame side cover; 20: simulation excavation hole; 21: first annular load sensor; 22: first pressure bearing cushion block; 23: first magnetostrictive displacement sensor; 24: second annular load sensor; 25: second pressure bearing cushion block; 26: second magnetostrictive displacement sensor; 27: first servo valve block; 28: first accumulator group; 29: second servo valve block; 30: second accumulator group; 31: dynamic fiber grating; 32: ultrasonic probe; 33: acoustic emission probe; 34: tunnel; 35: three-way acceleration sensor; 36: industrial endoscope; 37: industrial vacuum cleaner; 38: fault structural plane.

DETAILED DESCRIPTION OF THE PREFERRED EMBODIMENT

The invention will be further described in detail below with reference to the accompanying drawings and specific embodiments.

Figure 1:
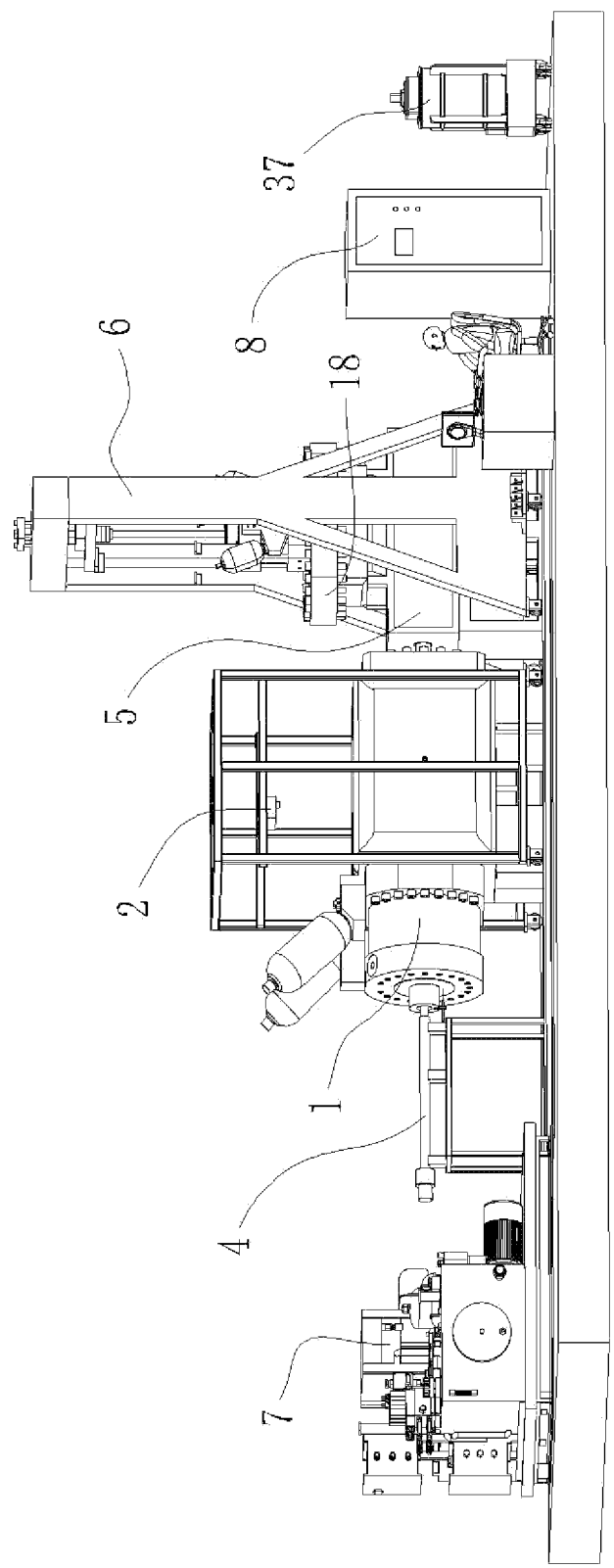
FIG. 1 is a schematic structural diagram of a large-scale three-dimensional physical simulation test system for the whole development process of deep engineering rock burst of the invention.
Figure 2:
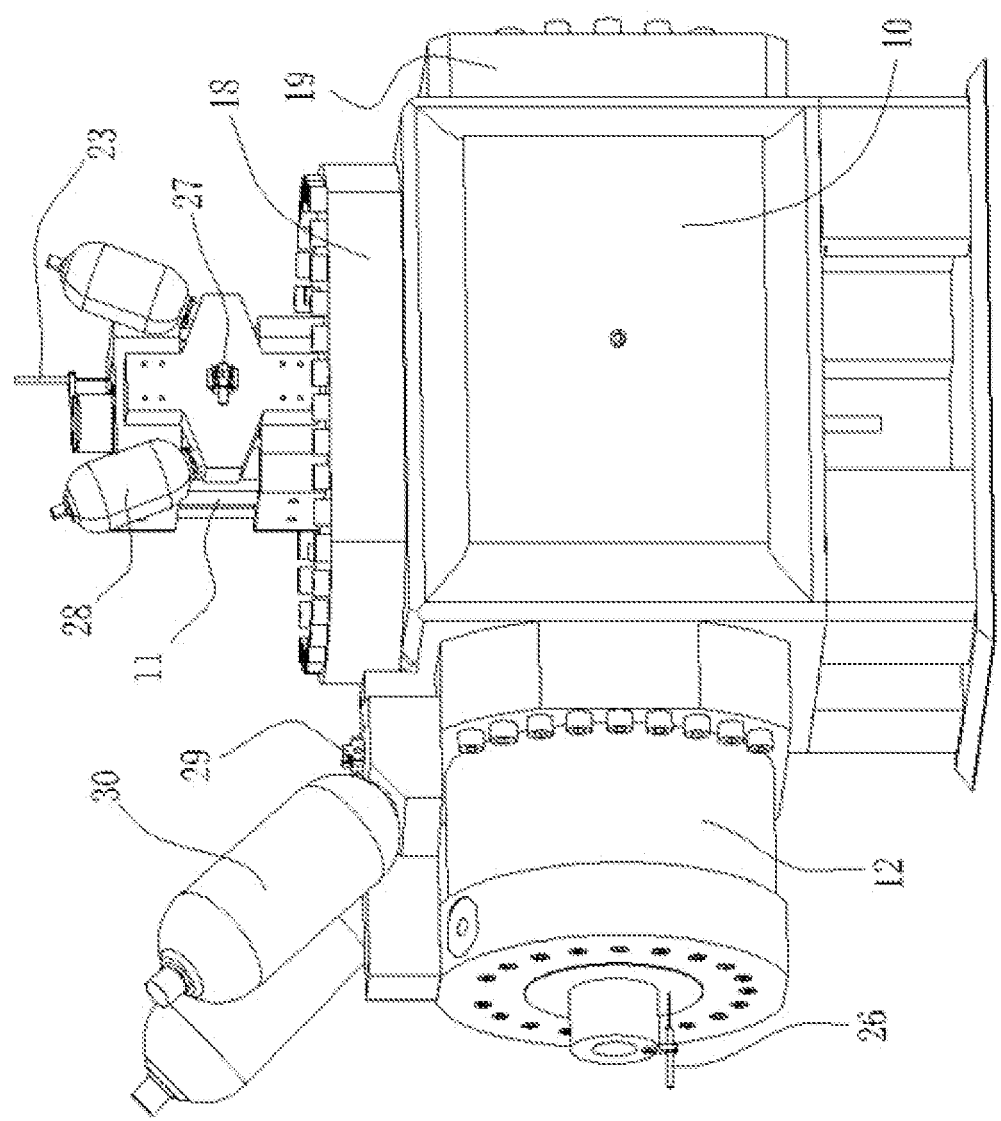
FIG. 2 is a schematic structural diagram (stereoscopic view) of the three-dimensional static stress loading device of the invention.
Figure 3:
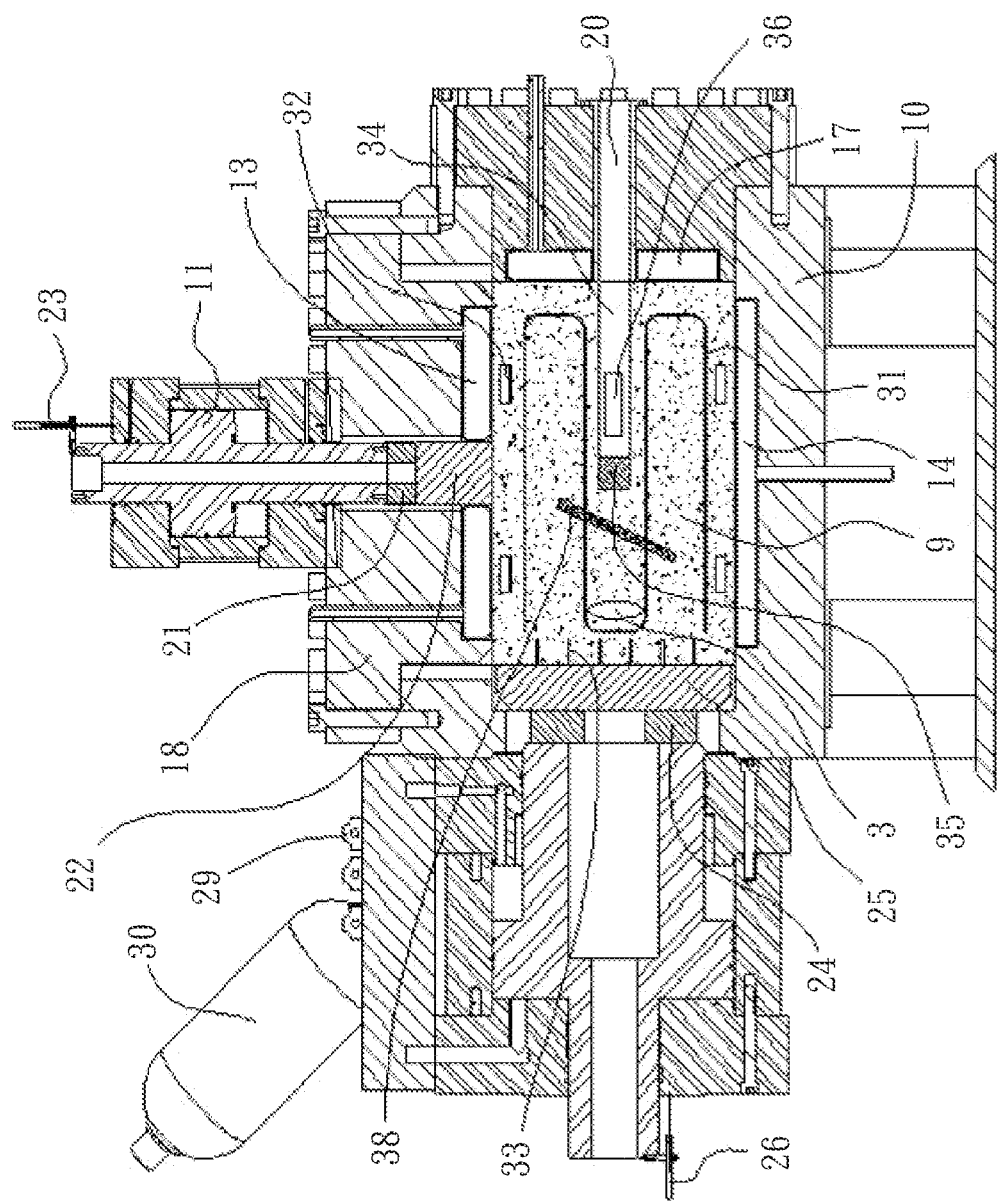
FIG. 3 is a schematic structural diagram (frontal cross-sectional view) of the three-dimensional static stress loading device of the invention.
Figure 4:
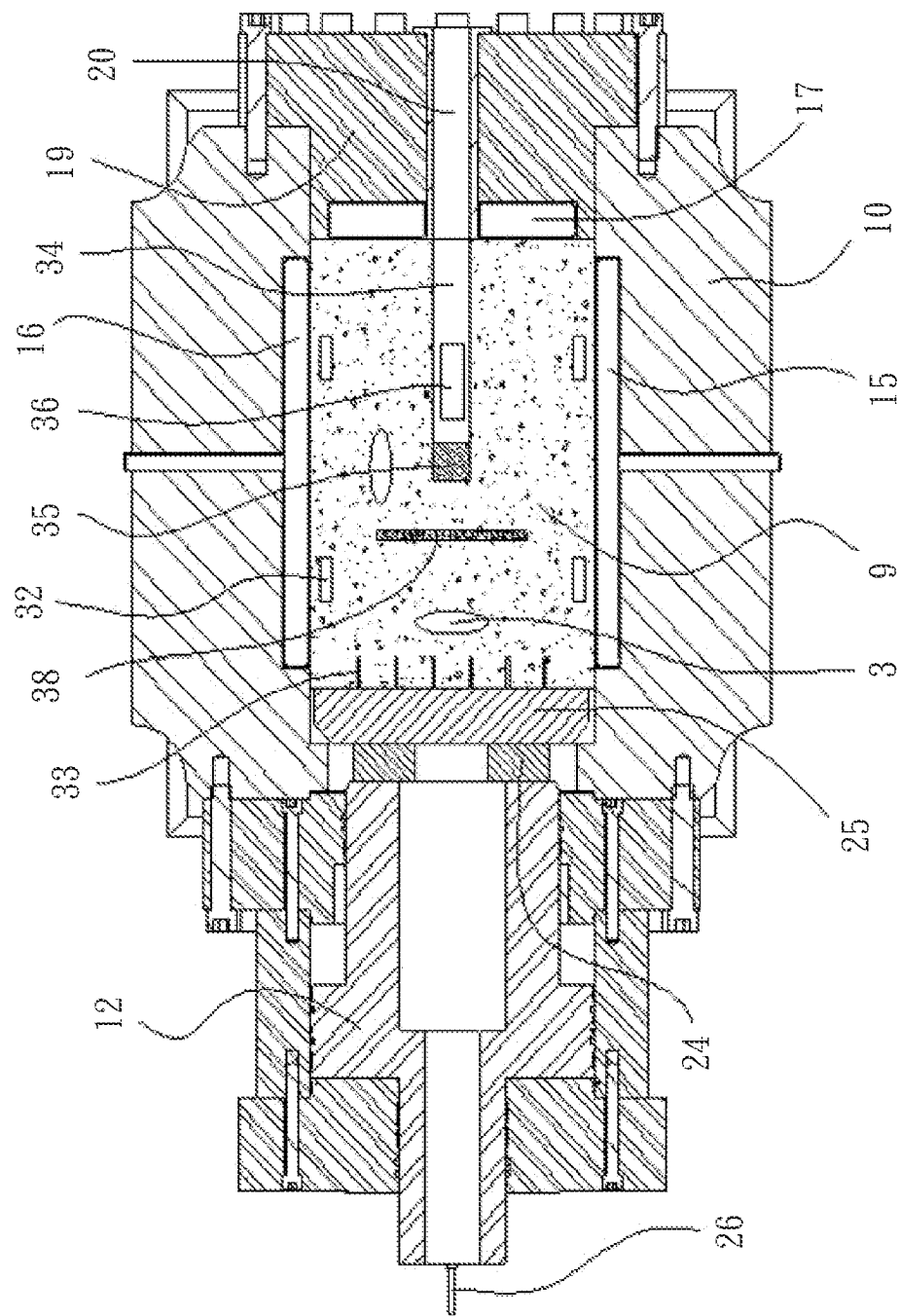
FIG. 4 is a schematic structural diagram (top cross-sectional view) of the three-dimensional static stress loading device of the invention.

As shown in FIGS. 1-4, a large-scale three-dimensional physical simulation test system for the whole development process of deep engineering rock burst comprises a three-dimensional static stress loading device 1, a 3D printer 2 for a physical model sample of similar materials, a $CO_2$ blast cracking device 3, a split Hopkinson pressure bar device 4, a miniature rotary excavation flexible mechanical arm device 5, a drop hammer impact device 6, a hydraulic oil source 7 and a controller 8. The $CO_2$ blast cracking device 3 is arranged in the physical model sample 9 of similar materials, and the physical model sample 9 of similar materials is located in the three-dimensional static stress loading device 1. The split Hopkinson pressure bar device 4 and the miniature rotary excavation flexible mechanical arm device 5 are arranged outside the three-dimensional static stress loading device 1, and the split Hopkinson pressure bar device 4, the three-dimensional static stress loading device 1 and the miniature rotary excavation flexible mechanical arm device 5 are arranged in a linear order and are all fixedly mounted on the ground. The 3D printer 2 for a physical model sample of similar materials is located outside the three-dimensional static stress loading device 1, and is mounted on the ground through a track movement structure, and a moving path of the 3D printer 2 for a physical model sample of similar materials passes through a position right above the three-dimensional static stress loading device 1. The drop hammer impact device 6 is located outside the three-dimensional static stress loading device 1 and is mounted on the ground through the track movement structure, and a moving path of the drop hammer impact device 6 passes through the position right above the three-dimensional static stress loading device 1. The hydraulic oil source 7 and the controller 8 are arranged outside the three-dimensional static stress loading device 1 and are both fixedly mounted on the ground, and the controller 8 is connected with a computer.

In the embodiments, the maximum static load applied by the three-dimensional static stress loading device 1 is 15 MPa, so that the self-gravity field of rock engineering with a buried depth of 5000 m can be equivalently simulated. The maximum impact height of the drop hammer rod of the drop hammer impact device 6 is 2 m, and the maximum impact energy is 500 J. The maximum initial velocity of the shock rod of the split Hopkinson pressure bar device 4 is 50 m/s, and the maximum shock pulse wave bandwidth is 0.1 MHz. The long-term load holding capacity of the hydraulic oil source 7 (hydraulic oil pump) is 8 months, and the hydraulic oil source 7 has the ability of automatically monitoring oil temperature, flow and oil pressure. The controller 8 has the ability of realizing sample stress control, deformation control, and cyclic loading and unloading control. The excavation manner of the miniature rotary excavation flexible mechanical arm device 5 is the same as that of the TBM, the diameter of a cutter head of the miniature rotary excavation flexible mechanical arm device 5 is 0.1 m, the advancing length is 0.8 m, the maximum advancing force is 32 kN, and the maximum rotary torque is 300 Nm.

The three-dimensional static stress loading device 1 comprises a high-rigidity three-dimensional reaction frame 10, a first dynamic hydraulic actuator 11, a second dynamic hydraulic actuator 12, a first flexible bladder hydraulic pillow 13, a second flexible bladder hydraulic pillow 14, a third flexible bladder hydraulic pillow 15, a fourth flexible bladder hydraulic pillow 16 and a fifth flexible bladder hydraulic pillow 17. The high-rigidity three-dimensional reaction frame 10 adopts an integral structure, and loading holes are respectively formed on the top, the left side and the right side of the high-rigidity three-dimensional reaction frame 10. A frame top cover 18 is fixedly mounted on the top of the high-rigidity three-dimensional reaction frame 10, and the first dynamic hydraulic actuator 11 is vertically and fixedly mounted at the center of the frame top cover 18. The second dynamic hydraulic actuator 12 is horizontally and fixedly mounted on the left side of the high-rigidity three-dimensional reaction frame 10. A frame side cover 19 is fixedly mounted on the right side of the high-rigidity three-dimensional reaction frame 10, and a simulation excavation hole 20 is formed at the center of the frame side cover 19. The first flexible bladder hydraulic pillow 13 is arranged on the lower surface of the frame top cover 18, and adopts a circular structure. The second flexible bladder hydraulic pillow 14 is arranged at the bottom of the high-rigidity three-dimensional reaction frame 10. The third flexible bladder hydraulic pillow 15 is arranged on the front side of the high-rigidity three-dimensional reaction frame 10. The fourth flexible bladder hydraulic pillow 16 is arranged on the rear side of the high-rigidity three-dimensional reaction frame 10. The fifth flexible bladder hydraulic pillow 17 is arranged on the inner surface of the frame side cover 19, and adopts the circular structure.

In the embodiments, the high-rigidity three-dimensional reaction frame 10 is manufactured by a process route of integral forging→roughing→heat treatment→finishing, and the overall rigidity is 10 GN/m. The rated load of the first dynamic hydraulic actuator 11 is 1000 kN, the rated load of the second dynamic hydraulic actuator 12 is 10000 kN, the diameter of each loading hole on the top, the left side and the right side of the high-rigidity three-dimensional reaction frame 10 is 900 mm, the diameter of the center hole of the frame top cover 18 is 200 mm, and the diameter of the simulation excavation hole 20 at the center of the frame side cover 19 is 100 mm. The first dynamic hydraulic actuator 11 and the second dynamic hydraulic actuator 12 use hydrostatic sealed dynamic hydraulic actuators to reduce the friction force of the piston rod. Piston rods of the first dynamic hydraulic actuator 11 and the second dynamic hydraulic actuator 12 are made of a light alloy material to achieve light weight to the greatest extent and reduce the influence of self-weight on the strain rate response during dynamic disturbance. The effective stroke of the first dynamic hydraulic actuator 11 and the second dynamic hydraulic actuator 12 is ±25 mm, a buffer zone is ±6 mm, and low frequency dynamic load capacity is 10 Hz.

The first flexible bladder hydraulic pillow 13 is connected with the hydraulic oil source 7 through a hydraulic oil path, and a first pressure sensor is arranged on the hydraulic oil path between the first flexible bladder hydraulic pillow 13 and the hydraulic oil source 7. The second flexible bladder hydraulic pillow 14 is connected with the hydraulic oil source 7 through the hydraulic oil path, and a second pressure sensor is arranged on the hydraulic oil path between the second flexible bladder hydraulic pillow 14 and the hydraulic oil source 7. The third flexible bladder hydraulic pillow 15 is connected with the hydraulic oil source 7 through the hydraulic oil path, and a third pressure sensor is arranged on the hydraulic oil path between the third flexible bladder hydraulic pillow 15 and the hydraulic oil source 7. The fourth flexible bladder hydraulic pillow 16 is connected with the hydraulic oil source 7 through the hydraulic oil path, and a fourth pressure sensor is arranged on the hydraulic oil path between the fourth flexible bladder hydraulic pillow 16 and the hydraulic oil source 7. The fifth flexible bladder hydraulic pillow 17 is connected with the hydraulic oil source 7 through the hydraulic oil path, and a fifth pressure sensor is arranged on the hydraulic oil path between the fifth flexible bladder hydraulic pillow 17 and the hydraulic oil source 7. Data output ends of the first pressure sensor, the second pressure sensor, the third pressure sensor, the fourth pressure sensor and the fifth pressure sensor are all electrically connected with the controller 8.

A piston rod of the first dynamic hydraulic actuator 11 adopts a hollow structure, and a first annular load sensor 21 and a first pressure bearing cushion block 22 are sequentially arranged between the piston rod of the first dynamic hydraulic actuator 11 and the physical model sample 9 of similar materials. A first magnetostrictive displacement sensor 23 is arranged between the piston rod of the first dynamic hydraulic actuator 11 and a cylinder cap. A piston rod of the second dynamic hydraulic actuator 12 adopts a hollow structure, and a second annular load sensor 24 and a second pressure bearing cushion block 25 are sequentially arranged between the piston rod of the second dynamic hydraulic actuator 12 and the physical model sample 9 of similar materials. A second magnetostrictive displacement sensor 26 is arranged between the piston rod of the second dynamic hydraulic actuator 12 and a cylinder cap. The first annular load sensor 21, the first magnetostrictive displacement sensor 23, the second annular load sensor 24 and the second magnetostrictive displacement sensor 26 are all electrically connected with the controller 8. In the embodiments, the first pressure bearing cushion block 22 can be a right-angled cushion block or an oblique cushion block. When the oblique cushion block is adopted, the oblique cushion block is used to form local stress concentration on the upper surface of the sample.

The hydraulic oil path of the first dynamic hydraulic actuator 11 is connected with the hydraulic oil source 7 through a first servo valve block 27, and first accumulator groups 28 are mounted on the first servo valve block 27. An electric control end of the first servo valve block 27 is electrically connected with the controller 8. The hydraulic oil path of the second dynamic hydraulic actuator 12 is connected with the hydraulic oil source 7 through second servo valve blocks 29, and second accumulator groups 30 are respectively mounted on the second servo valve blocks 29. An electric control end of the second servo valve block 29 is electrically connected with the controller 8.

An emission rod of the split Hopkinson pressure bar device 4 sequentially passes through a center hole of the piston rod of the second dynamic hydraulic actuator 12 and a center hole of the second annular load sensor 24 to be opposite to the second pressure bearing cushion block 25. A mechanical arm of the miniature rotary excavation flexible mechanical arm device 5 sequentially passes through the simulation excavation hole 20 and a center hole of the fifth flexible bladder hydraulic pillow 17 to be opposite to the physical model sample 9 of similar materials. A drop hammer rod of the drop hammer impact device 6 sequentially passes through the center hole of the piston rod of the first dynamic hydraulic actuator 11 and the center hole of the first annular load sensor 21 to be opposite to the first pressure bearing cushion block 22.

A dynamic fiber grating 31 and ultrasonic probes 32 are respectively pre-embedded in the physical model sample 9 of similar materials, acoustic emission probes 33 are pre-installed on the boundary of the physical model sample 9 of similar materials, and signal output ends of the dynamic fiber grating 31, the ultrasonic probes 32 and the acoustic emission probes 33 are all electrically connected with the controller 8. After excavation of the tunnel 34 is completed in the physical model sample 9 of similar materials, a three-way acceleration sensor 35 and an industrial endoscope 36 are arranged in the tunnel 34.

When carrying out an immediate strain burst simulation test, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover 18 with the high-rigidity three-dimensional reaction frame 10, then moving the drop hammer impact device 6 to a position right above the high-rigidity three-dimensional reaction frame 10, lifting the frame top cover 18 by the drop hammer impact device 6, and then moving the drop hammer impact device 6 hanging the frame top cover 18 away from the position right above the high-rigidity three-dimensional reaction frame 10;

Step III: moving the 3D printer 2 for the physical model sample of similar materials to the position right above the high-rigidity three-dimensional reaction frame 10, using the prepared similar materials as a printing raw material of the 3D printer 2 for the physical model sample of similar materials, completing in-situ printing of the physical model sample 9 of similar materials in the high-rigidity three-dimensional reaction frame 10 through the 3D printer 2 for the physical model sample 9 of similar materials, and during the printing process, pre-embedding the dynamic fiber grating 31 and the ultrasonic probes 32 at internal set positions in the physical model sample 9 of similar materials, and pre-mounting the acoustic emission probes 33 at set positions on the boundary of the physical model sample 9 of similar materials, in the embodiment, the printed physical model sample 9 of similar materials is a cuboid of 1.2 m×1 m×1 m;

Step IV: performing in-situ normal temperature curing on the printed physical model sample 9 of similar materials for the curing period of 28 days, after the curing period is over, detecting whether the flatness, the verticality and the compactness of the physical model sample 9 of similar materials are qualified, if the flatness, the verticality and the compactness are qualified, detecting whether the dynamic fiber grating 31, the ultrasonic probes 32 and the acoustic emission probes 33 on the boundary, pre-embedded in the physical model sample 9 of similar materials work normally or not, if they work normally, moving the drop hammer impact device 6 hanging the frame top cover 18 to the position right above the high-rigidity three-dimensional reaction frame 10, and then enabling the frame top cover 18 to drop back to the top of the high-rigidity three-dimensional reaction frame 10 through the drop hammer impact device 6, and reconnecting the frame top cover 18 with the high-rigidity three-dimensional reaction frame 10 together, and then moving the drop hammer impact device 6 away from the position right above the high-rigidity three-dimensional reaction frame 10;

Step VI: adopting the stress control manner, synchronously controlling the first dynamic hydraulic actuator 11, the first flexible bladder hydraulic pillow 13 and the second flexible bladder hydraulic pillow 14 to apply prestress to the physical model sample 9 of similar materials to realize target value until prestressed loading in the maximum principal stress direction is completed, in the embodiment, the target value of the prestress is 0.5 MPa, and the loading rate is 0.01 MPa/s;

Step VI: adopting the stress control manner, synchronously controlling the third flexible bladder hydraulic pillow 15 and the fourth flexible bladder hydraulic pillow 16 to apply prestress to the physical model sample 9 of similar materials to realize target value until prestressed loading in the intermediate principal stress direction is completed, in the embodiment, the target value of the prestress is 0.5 MPa, and the loading rate is 0.01 MPa/s;

Step VI: adopting the stress control manner, synchronously controlling the second dynamic hydraulic actuator 12 and fifth flexible bladder hydraulic pillow 17 to apply prestress to the physical model sample 9 of similar materials to realize target value until prestressed loading in the minimum principal stress direction is completed, in the embodiment, the target value of the prestress is 0.5 MPa, and the loading rate is 0.01 MPa/s;

Step VIII: adopting the stress control manner, firstly loading the physical model sample 9 of similar materials to the target value of minimum principal stress through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17, and then continuing to load the physical model sample 9 of similar materials to the target value of intermediate principal stress through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16, and finally, continuing to load the physical model sample 9 of similar materials to the target value of maximum principal stress through the first dynamic hydraulic actuator 11, the first flexible bladder hydraulic pillow 13 and the second flexible bladder hydraulic pillow 14, in the embodiment, the target value of the minimum principal stress is 3 MPa, the target value of the intermediate principal stress is 5 MPa, the target value of the maximum principal stress is 15 MPa, and the loading rate is 0.05 MPa/s;

Step IX: starting the miniature rotary excavation flexible mechanical arm device 5, controlling the mechanical arm of the miniature rotary excavation flexible mechanical arm device 5 to sequentially penetrate through the simulation excavation hole 20 and the center hole of the fifth flexible bladder hydraulic pillow 17, and starting excavating on the physical model sample 9 of similar materials in the minimum principal stress direction until processing of the tunnel 34 is finished, in the embodiment, the target depth of the tunnel 34 in the model sample is 0.5 m, and the excavation is completed in five times, and thus the depth of each excavation is 0.1 m, and it is necessary to use the industrial vacuum cleaner 37 to remove fragments generated after the excavation;

Step X: closing the miniature rotary excavation flexible mechanical arm device 5, firstly enabling the mechanical arm of the miniature rotary excavation flexible mechanical arm device 5 to exit from the tunnel 34, the center hole of the fifth flexible bladder hydraulic pillow 17 and the simulation excavation hole 20, and then sequentially sending the three-way acceleration sensor 35 and the industrial endoscope 36 into the tunnel 34, monitoring acceleration data of an elastic wave of the surrounding rock of the wall of the tunnel 34 through the three-way acceleration sensor 35, and monitoring the damage of the surrounding rock of the wall of the tunnel 34 through the industrial endoscope 36, in the embodiment, since the tunnel 34 is excavated in five times, after each excavation is completed, the three-way acceleration sensor 35 and the industrial endoscope 36 both need to monitor the surrounding rock of the wall of the tunnel 34 once;

Step XI: performing static stress holding on the physical model sample 9 of similar materials after excavation of the tunnel 34 is finished, in the embodiment, the static stress holding time is 30 minutes, and in the static stress holding process, a slight immediate strain rock burst can occur;

Step XII: after the static stress holding is over, applying disturbance loads based on static pressure of target value of maximum principal stress through the first dynamic hydraulic actuator 11 to induce immediate strain burst, and during the process of applying the disturbance loads, monitoring internal deformation of the physical model sample 9 of similar materials through the dynamic fiber grating 31, monitoring the wave velocity of the physical model sample 9 of similar materials in the loading process through the ultrasonic probes 32, and monitoring acoustic emission signals of the physical model sample 9 of similar materials in the loading process through the acoustic emission probes 33, and in the embodiment, the frequency of the disturbance loads is 5 Hz, the amplitude of the disturbance loads is 300 kN, the application time of the disturbance loads is 30 minutes, and a high-strength immediate strain burst occurs in the physical model sample 9 of similar materials in this process; and Step XIII: after rock burst occurs, firstly, unloading the loads applied to the physical model sample 9 of similar materials through the first dynamic hydraulic actuator 11, the first flexible bladder hydraulic pillow 13 and the second flexible bladder hydraulic pillow 14 to the target value of the intermediate principal stress, and then unloading the loads applied to the physical model sample 9 of similar materials through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16 to the target value of the minimum principal stress, and finally, unloading the loads applied to the physical model sample 9 of similar materials through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17 to 0. In the embodiment, the target value of the minimum principal stress is 3 MPa, the target value of the intermediate principal stress is 5 MPa, and the unloading rate is 0.5 MPa/s.

When carrying out an immediate strain-structural rock burst simulation test, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover 18 with the high-rigidity three-dimensional reaction frame 10, then moving the drop hammer impact device 6 to a position right above the high-rigidity three-dimensional reaction frame 10, lifting the frame top cover 18 by the drop hammer impact device 6, and then moving the drop hammer impact device 6 hanging the frame top cover 18 away from the position right above the high-rigidity three-dimensional reaction frame 10;

Step III: moving the 3D printer 2 for the physical model sample of similar materials to the position right above the high-rigidity three-dimensional reaction frame 10, using the prepared similar materials as a printing raw material of the 3D printer 2 for the physical model sample of similar materials, completing in-situ printing of the physical model sample 9 of similar materials in the high-rigidity three-dimensional reaction frame 10 through the 3D printer 2 for the physical model sample 9 of similar materials, and during the printing process, pre-embedding the $CO_2$ blast cracking device 3, the dynamic fiber grating 31 and the ultrasonic probes 32 at internal set positions in the physical model sample 9 of similar materials, and pre-mounting the acoustic emission probes 33 at set positions on the boundary of the physical model sample 9 of similar materials, at the same time, printing a fault structural plane 38 in the physical model sample 9 of similar materials, wherein the pre-embedded position of the $CO_2$ blast cracking device 3 is located above the center of the fault structural plane 38, in the embodiment, the printed physical model sample 9 of similar materials is a cuboid of 1.2 m×1 m×1 m, the inclination angle of the fault structural plane 38 is 45°, the length of the fault structural plane 38 is 0.6 m, and the width of the fault structural plane 38 is 0.02 m;

Step IV: performing in-situ normal temperature curing on the printed physical model sample 9 of similar materials for the curing period of 28 days, after the curing period is over, detecting whether the flatness, the verticality and the compactness of the physical model sample 9 of similar materials are qualified, if the flatness, the verticality and the compactness are qualified, detecting whether the dynamic fiber grating 31, the ultrasonic probes 32 and the acoustic emission probes 33 on the boundary, pre-embedded in the physical model sample 9 of similar materials work normally or not, if they work normally, moving the drop hammer impact device 6 hanging the frame top cover 18 to the position right above the high-rigidity three-dimensional reaction frame 10, and enabling the frame top cover 18 to drop back to the top of the high-rigidity three-dimensional reaction frame 10 through the drop hammer impact device 6, and reconnecting the frame top cover 18 with the high-rigidity three-dimensional reaction frame 10 together, and then moving the drop hammer impact device 6 away from the position right above the high-rigidity three-dimensional reaction frame 10;

Step VI: adopting the stress control manner, synchronously controlling the first dynamic hydraulic actuator 11, the first flexible bladder hydraulic pillow 13 and the second flexible bladder hydraulic pillow 14 to apply prestress to the physical model sample 9 of similar materials to realize target value until prestressed loading in the maximum principal stress direction is completed, in the embodiment, the target value of the prestress is 0.5 MPa, and the loading rate is 0.01 MPa/s;

Step VI: adopting the stress control manner, synchronously controlling the third flexible bladder hydraulic pillow 15 and the fourth flexible bladder hydraulic pillow 16 to apply prestress to the physical model sample 9 of similar materials to realize target value until prestressed loading in the intermediate principal stress direction is completed, in the embodiment, the target value of the prestress is 0.5 MPa, and the loading rate is 0.01 MPa/s;

Step VI: adopting the stress control manner, synchronously controlling the second dynamic hydraulic actuator 12 and fifth flexible bladder hydraulic pillow 17 to apply prestress to the physical model sample 9 of similar materials to realize target value until prestressed loading in the minimum principal stress direction is completed, in the embodiment, the target value of the prestress is 0.5 MPa, and the loading rate is 0.01 MPa/s;

Step VIII: adopting the stress control manner, firstly loading the physical model sample 9 of similar materials to the target value of minimum principal stress through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17, and then continuing to load the physical model sample 9 of similar materials to the target value of intermediate principal stress through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16, and finally, continuing to load the physical model sample 9 of similar materials to the target value of maximum principal stress through the first dynamic hydraulic actuator 11, the first flexible bladder hydraulic pillow 13 and the second flexible bladder hydraulic pillow 14, in the embodiment, the target value of the minimum principal stress is 3 MPa, the target value of the intermediate principal stress is 5 MPa, the target value of the maximum principal stress is 15 MPa, and the loading rate is 0.05 MPa/s;

Step IX: starting the miniature rotary excavation flexible mechanical arm device 5, controlling the mechanical arm of the miniature rotary excavation flexible mechanical arm device 5 to sequentially penetrate through the simulation excavation hole 20 and the center hole of the fifth flexible bladder hydraulic pillow 17, and starting excavating on the physical model sample 9 of similar materials in the minimum principal stress direction until processing of the tunnel 34 is finished, in the embodiment, the target depth of the tunnel 34 is 0.5 m, the excavation is completed in five times, the depth of each excavation is 0.1 m, and it is necessary to use the industrial vacuum cleaner 37 to remove fragments generated after the excavation;

Step X: closing the miniature rotary excavation flexible mechanical arm device 5, firstly enabling a drill rod of the miniature rotary excavation flexible mechanical arm device 5 to exit from the tunnel 34, the center hole of the fifth flexible bladder hydraulic pillow 17 and the simulation excavation hole 20, and then sequentially sending the three-way acceleration sensor 35 and the industrial endoscope 36 into the tunnel 34, monitoring acceleration data of an elastic wave of the surrounding rock of the wall of the tunnel 34 through the three-way acceleration sensor 35, and monitoring the damage of the surrounding rock of the wall of the tunnel 34 through the industrial endoscope 36, in the embodiment, since the tunnel 34 is excavated in five times, after each excavation is completed, the three-way acceleration sensor 35 and the industrial endoscope 36 both need to monitor the surrounding rock of the wall of the tunnel 34 once;

Step XI: performing static stress holding on the physical model sample 9 of similar materials after excavation of the tunnel 34 is finished, in the embodiment, the static stress holding time is 30 minutes, and during the static stress holding process, a slight immediate strain-structural rock burst can occur;

Step XII: after the static stress holding is over, applying disturbance loads based on static pressure of target value of maximum principal stress through the first dynamic hydraulic actuator 11, and at the same time, starting the $CO_2$ blast cracking device 3 to apply burst impact to the physical model sample 9 of similar materials to induce immediate strain-structural rock burst, and during the process of applying the disturbance loads and the burst impact, monitoring internal deformation of the physical model sample 9 of similar materials through the dynamic fiber grating 31, monitoring the wave velocity of the physical model sample 9 of similar materials in the loading process through the ultrasonic probes 32, and monitoring acoustic emission signals of the physical model sample 9 of similar materials in the loading process through the acoustic emission probes 33, in the embodiment, the frequency of the disturbance loads is 10 Hz, the amplitude of the disturbance loads is 300 kN, the application time of the disturbance loads is 30 minutes, and a high-strength immediate strain-structural rock burst occurs in the physical model sample 9 of similar materials in this process; and Step XIII: after rock burst occurs, firstly, unloading the loads applied to the physical model sample 9 of similar materials through the first dynamic hydraulic actuator 11, the first flexible bladder hydraulic pillow 13 and the second flexible bladder hydraulic pillow 14 to the target value of the intermediate principal stress, and then unloading the loads applied to the physical model sample 9 of similar materials through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16 to the target value of the minimum principal stress, and finally, unloading the loads applied to the physical model sample 9 of similar materials through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17 to 0. In the embodiment, the target value of the minimum principal stress is 3 MPa, the target value of the intermediate principal stress is 5 MPa, and the unloading rate is 0.5 MPa/s.

when carrying out time delayed rock burst simulation test, the following steps are included:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover 18 with the high-rigidity three-dimensional reaction frame 10, and then moving the drop hammer impact device 6 to a position right above the high-rigidity three-dimensional reaction frame 10, lifting the frame top cover 18 by the drop hammer impact device 6, and then moving the drop hammer impact device 6 hanging the frame top cover 18 away from the position right above the high-rigidity three-dimensional reaction frame 10;

Step III: moving the 3D printer 2 for the physical model sample of similar materials to the position right above the high-rigidity three-dimensional reaction frame 10, using the prepared similar materials as a printing raw material of the 3D printer 2 for the physical model sample of similar materials, completing in-situ printing of the physical model sample 9 of similar materials in the high-rigidity three-dimensional reaction frame 10 through the 3D printer 2 for the physical model sample 9 of similar materials, and during the printing process, pre-embedding the dynamic fiber grating 31 and the ultrasonic probes 32 at internal set positions in the physical model sample 9 of similar materials, and pre-mounting the acoustic emission probes 33 at set positions on the boundary of the physical model sample 9 of similar materials, in the embodiment, the printed physical model sample 9 of similar materials is a cuboid of 1.2 m×1 m×1 m;

Step IV: performing in-situ normal temperature curing on the printed physical model sample 9 of similar materials for the curing period of 28 days, after the curing period is over, detecting whether the flatness, the verticality and the compactness of the physical model sample 9 of similar materials are qualified, if the flatness, the verticality and the compactness are qualified, detecting whether the dynamic fiber grating 31, the ultrasonic probes 32 and the acoustic emission probes 33 on the boundary, pre-embedded in the physical model sample 9 of similar materials work normally or not, if they work normally, moving the drop hammer impact device 6 hanging the frame top cover 18 to the position right above the high-rigidity three-dimensional reaction frame 10, and then enabling the frame top cover 18 to drop back to the top of the high-rigidity three-dimensional reaction frame 10 through the drop hammer impact device 6, and reconnecting the frame top cover 18 with the high-rigidity three-dimensional reaction frame 10 together, and then moving the drop hammer impact device 6 away from the position right above the high-rigidity three-dimensional reaction frame 10;

Step VI: adopting the stress control manner, synchronously controlling the first dynamic hydraulic actuator 11, the first flexible bladder hydraulic pillow 13 and the second flexible bladder hydraulic pillow 14 to apply prestress to the physical model sample 9 of similar materials to realize target value until prestressed loading in the maximum principal stress direction is completed, in the embodiment, the target value of the prestress is 0.5 MPa, and the loading rate is 0.01 MPa/s;

Step VI: adopting the stress control manner, synchronously controlling the third flexible bladder hydraulic pillow 15 and the fourth flexible bladder hydraulic pillow 16 to apply prestress to the physical model sample 9 of similar materials to realize target value until prestressed loading in the intermediate principal stress direction is completed, in the embodiment, the target value of the prestress is 0.5 MPa, and the loading rate is 0.01 MPa/s;

Step VI: adopting the stress control manner, synchronously controlling the second dynamic hydraulic actuator 12 and fifth flexible bladder hydraulic pillow 17 to apply prestress to the physical model sample 9 of similar materials, and then apply prestress to the physical model sample 9 of similar materials to realize target value until prestressed loading in the minimum principal stress direction is completed, in the embodiment, the target value of the prestress is 0.5 MPa, and the loading rate is 0.01 MPa/s;

Step VIII: adopting the stress control manner, firstly loading the physical model sample 9 of similar materials to the target value of minimum principal stress through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17, and then continuing to load the physical model sample 9 of similar materials to the target value of intermediate principal stress through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16, and finally, continuing to load the physical model sample 9 of similar materials to the target value of maximum principal stress through the first dynamic hydraulic actuator 11, the first flexible bladder hydraulic pillow 13 and the second flexible bladder hydraulic pillow 14, in the embodiment, the target value of the minimum principal stress is 3 MPa, the target value of the intermediate principal stress is 5 MPa, the target value of the maximum principal stress is 8 MPa, and the loading rate is 0.05 MPa/s;

Step IX: starting the miniature rotary excavation flexible mechanical arm device 5, controlling the mechanical arm of the miniature rotary excavation flexible mechanical arm device 5 to sequentially penetrate through the simulation excavation hole 20 and the center hole of the fifth flexible bladder hydraulic pillow 17, and starting excavating on the physical model sample 9 of similar materials in the minimum principal stress direction until processing of the tunnel 34 is finished, in the embodiment, the target depth of the tunnel 34 is 0.5 m, the excavation is completed in five times, the depth of each excavation is 0.1 m, and it is necessary to use the industrial vacuum cleaner 37 to remove fragments generated after the excavation;

Step X: closing the miniature rotary excavation flexible mechanical arm device 5, firstly enabling the mechanical arm of the miniature rotary excavation flexible mechanical arm device 5 to exit from the tunnel 34, the center hole of the fifth flexible bladder hydraulic pillow 17 and the simulation excavation hole 20, and then sequentially sending the three-way acceleration sensor 35 and the industrial endoscope 36 into the tunnel 34, monitoring acceleration data of an elastic wave of the surrounding rock of the wall of the tunnel 34 through the three-way acceleration sensor 35, and monitoring the damage of the surrounding rock of the wall of the tunnel 34 through the industrial endoscope 36, in the embodiment, since the tunnel 34 is excavated in five times, after each excavation is completed, the three-way acceleration sensor 35 and the industrial endoscope 36 both need to monitor the surrounding rock of the wall of the tunnel 34 once;

Step XI: performing static stress holding on the physical model sample 9 of similar materials after excavation of the tunnel 34 is finished, in the embodiment, the static stress holding time is 5 months;

Step XII: after the static stress holding is over, applying disturbance loads based on static pressure of target value of maximum principal stress through the first dynamic hydraulic actuator 11 to induce low-intensity time delayed rock burst, and then starting the drop hammer impact device 6, so that the drop hammer rod of the drop hammer impact device 6 freely drops down and impacts the first pressure bearing cushion block 22, and application of external disturbances is finished to induce middle-intensity time delayed rock burst, and finally, starting the split Hopkinson pressure bar device 4, so that the emission rod of the split Hopkinson pressure bar device 4 impacts the second pressure bearing cushion block 25 to complete further application of the external disturbances in order to induce high-intensity time delayed rock burst, and during the process of applying the disturbance loads, monitoring deformation of the physical model sample 9 of similar materials through the dynamic fiber grating 31, monitoring the wave velocity of the physical model sample 9 of similar materials in the loading process through the ultrasonic probes 32, and monitoring acoustic emission signals of the physical model sample 9 of similar materials in the loading process through the acoustic emission probes 33, in the embodiment, the frequency of the disturbance loads is 5 Hz, the amplitude of the disturbance loads is 300 kN, and the application time of the disturbance loads is 60 minutes, and the drop height of the drop hammer rod of the drop hammer impact device 6 is 1.5 m, and the number of times of drop and impact of the drop hammer rod of the drop hammer impact device 6 is 5 times, so that the initial velocity of the emission rod of the split Hopkinson pressure bar device 4 is 1 m/s, and the number of times of emitting, drop and impact is 5 times; and Step XIII: after rock burst occurs, firstly, unloading the loads applied to the physical model sample 9 of similar materials through the first dynamic hydraulic actuator 11, the first flexible bladder hydraulic pillow 13 and the second flexible bladder hydraulic pillow 14 to the target value of the intermediate principal stress, and then unloading the loads applied to the physical model sample 9 of similar materials through the first dynamic hydraulic actuator 11, the first flexible bladder hydraulic pillow 13, the second flexible bladder hydraulic pillow 14, the third flexible bladder hydraulic pillow 15 and the fourth flexible bladder hydraulic pillow 16 to the target value of the minimum principal stress, and finally, unloading the loads applied to the physical model sample 9 of similar materials through the first dynamic hydraulic actuator 11, the second dynamic hydraulic actuator 12, the first flexible bladder hydraulic pillow 13, the second flexible bladder hydraulic pillow 14, the third flexible bladder hydraulic pillow 15, the fourth flexible bladder hydraulic pillow 16 and the fifth flexible bladder hydraulic pillow 17 to 0. In the embodiment, the target value of the minimum principal stress is 3 MPa, the target value of the intermediate principal stress is 5 MPa, and the unloading rate is 0.5 MPa/s.

The schemes in the embodiments are not intended to limit the scope of claims of the invention, and all equivalent implementations or modifications that do not depart from the invention are included in the scope of claims of the present application.

What is claimed is:

1. A large-scale three-dimensional physical simulation test system for a whole development process of a deep engineering rock burst, comprising: a three-dimensional static stress loading device, a 3D printer for a physical model sample of similar materials, a $CO_2$ blast cracking device, a split Hopkinson pressure bar device, a miniature rotary excavation flexible mechanical arm device, a drop hammer impact device, a hydraulic oil source and a controller,
   wherein the $CO_2$ blast cracking device is arranged in the physical model sample of similar materials, and the physical model sample of similar materials is located in the three-dimensional static stress loading device,
   the split Hopkinson pressure bar device and the miniature rotary excavation flexible mechanical arm device are arranged outside the three-dimensional static stress loading device, and the split Hopkinson pressure bar device, the three-dimensional static stress loading device and the miniature rotary excavation flexible mechanical arm device are arranged in a linear order and all of them are fixedly mounted on the ground,
   the 3D printer for the physical model sample of similar materials is located outside the three-dimensional static stress loading device, and is mounted on the ground through a track movement structure, and a moving path of the 3D printer for the physical model sample of similar materials passes through a position right above the three-dimensional static stress loading device,
   the drop hammer impact device is located outside the three-dimensional static stress loading device and is mounted on the ground through the track movement structure, and a moving path of the drop hammer impact device passes through the position right above the three-dimensional static stress loading device, and
   the hydraulic oil source and the controller are arranged outside the three-dimensional static stress loading device and both are fixedly mounted on the ground, and the controller is connected with a computer.

2. The large-scale three-dimensional physical simulation test system according to claim 1, wherein the three-dimensional static stress loading device comprises a high-rigidity three-dimensional reaction frame, a first dynamic hydraulic actuator, a second dynamic hydraulic actuator, a first flexible bladder hydraulic pillow, a second flexible bladder hydraulic pillow, a third flexible bladder hydraulic pillow, a fourth flexible bladder hydraulic pillow and a fifth flexible bladder hydraulic pillow, and
   wherein the high-rigidity three-dimensional reaction frame adopts an integral structure, and loading holes are respectively formed on the top, the left side and the right side of the high-rigidity three-dimensional reaction frame,
   a frame top cover is fixedly mounted on the top of the high-rigidity three-dimensional reaction frame, and the first dynamic hydraulic actuator is vertically and fixedly mounted at the center of the frame top cover,
   the second dynamic hydraulic actuator is horizontally and fixedly mounted on the left side of the high-rigidity three-dimensional reaction frame,
   a frame side cover is fixedly mounted on the right side of the high-rigidity three-dimensional reaction frame, and a simulation excavation hole is formed at the center of the frame side cover,
   the first flexible bladder hydraulic pillow is arranged on the lower surface of the frame top cover, and adopts a circular structure,
   the second flexible bladder hydraulic pillow is arranged at the bottom of the high-rigidity three-dimensional reaction frame,
   the third flexible bladder hydraulic pillow is arranged on the front side of the high-rigidity three-dimensional reaction frame,
   the fourth flexible bladder hydraulic pillow is arranged on the rear side of the high-rigidity three-dimensional reaction frame, and
   the fifth flexible bladder hydraulic pillow is arranged on the inner surface of the frame side cover, and adopts the circular structure.

3. The large-scale three-dimensional physical simulation test system according to claim 2, wherein the first flexible bladder hydraulic pillow is connected with the hydraulic oil source through a hydraulic oil path, and a first pressure sensor is arranged on the hydraulic oil path between the first flexible bladder hydraulic pillow and the hydraulic oil source,
the second flexible bladder hydraulic pillow is connected with the hydraulic oil source through the hydraulic oil path, and a second pressure sensor is arranged on the hydraulic oil path between the second flexible bladder hydraulic pillow and the hydraulic oil source,
the third flexible bladder hydraulic pillow is connected with the hydraulic oil source through the hydraulic oil path, and a third pressure sensor is arranged on the hydraulic oil path between the third flexible bladder hydraulic pillow and the hydraulic oil source,
the fourth flexible bladder hydraulic pillow is connected with the hydraulic oil source through the hydraulic oil path, and a fourth pressure sensor is arranged on the hydraulic oil path between the fourth flexible bladder hydraulic pillow and the hydraulic oil source,
the fifth flexible bladder hydraulic pillow is connected with the hydraulic oil source through the hydraulic oil path, and a fifth pressure sensor is arranged on the hydraulic oil path between the fifth flexible bladder hydraulic pillow and the hydraulic oil source, and
data output ends of the first pressure sensor, the second pressure sensor, the third pressure sensor, the fourth pressure sensor and the fifth pressure sensor are all electrically connected with the controller.

4. The large-scale three-dimensional physical simulation test system according to claim 3, wherein a piston rod of the first dynamic hydraulic actuator adopts a hollow structure, and a first annular load sensor and a first pressure bearing cushion block are sequentially arranged between the piston rod of the first dynamic hydraulic actuator and the physical model sample of similar materials,
a first magnetostrictive displacement sensor is arranged between the piston rod of the first dynamic hydraulic actuator and its cylinder cap,
a piston rod of the second dynamic hydraulic actuator adopts a hollow structure, and a second annular load sensor and a second pressure bearing cushion block are sequentially arranged between the piston rod of the second dynamic hydraulic actuator and the physical model sample of similar materials,
a second magnetostrictive displacement sensor is arranged between the piston rod of the second dynamic hydraulic actuator and its cylinder cap, and
the first annular load sensor, the first magnetostrictive displacement sensor, the second annular load sensor and the second magnetostrictive displacement sensor are all electrically connected with the controller.

5. The large-scale three-dimensional physical simulation test system according to claim 4, wherein the hydraulic oil path of the first dynamic hydraulic actuator is connected with the hydraulic oil source through a first servo valve block, and first accumulator groups are mounted on the first servo valve block,
an electric control end of the first servo valve block is electrically connected with the controller,
the hydraulic oil path of the second dynamic hydraulic actuator is connected with the hydraulic oil source through second servo valve blocks, and second accumulator groups are respectively mounted on the second servo valve blocks, and
electric control ends of the second servo valve blocks are electrically connected with the controller.

6. The large-scale three-dimensional physical simulation test system according to claim 5, wherein an emission rod of the split Hopkinson pressure bar device sequentially passes through a center hole of the piston rod of the second dynamic hydraulic actuator and a center hole of the second annular load sensor to be opposite to the second pressure bearing cushion block,
a mechanical arm of the miniature rotary excavation flexible mechanical arm device sequentially passes through the simulation excavation hole and a center hole of the fifth flexible bladder hydraulic pillow to be opposite to the physical model sample of similar materials, and
a drop hammer rod of the drop hammer impact device sequentially passes through the center hole of the piston rod of the first dynamic hydraulic actuator and the center hole of the first annular load sensor to be opposite to the first pressure bearing cushion block.

7. The large-scale three-dimensional physical simulation test system according to claim 6, wherein a dynamic fiber grating and ultrasonic probes are respectively pre-embedded in the physical model sample of similar materials, acoustic emission probes are pre-installed on the boundary of the physical model sample of similar materials, and signal output ends of the dynamic fiber grating, the ultrasonic probes and the acoustic emission probes are all electrically connected with the controller, and
after excavation of a tunnel is completed in the physical model sample of similar materials, a three-way acceleration sensor and an industrial endoscope are arranged in the tunnel.

8. The large-scale three-dimensional physical simulation test system according to claim 7, wherein, carrying out an immediate strain burst simulation test includes the following steps:
Step I: preparing the similar materials, wherein the similar materials comprise the raw materials of water, barite powder, borax, gypsum, cement and a rosin alcohol solution in the ratio of 25% to 20% to 20% to 20% to 10% to 5%;
Step II: disconnecting the frame top cover with the high-rigidity three-dimensional reaction frame, and then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;
Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during a printing process, pre-embedding the dynamic fiber grating and the ultrasonic probes at internal set positions in the physical model sample of similar materials, and pre-mounting the acoustic emission probes at set positions on the boundary of the physical model sample of similar materials;

Step IV: performing in-situ normal temperature curing on the printed physical model sample of similar materials, after a curing period is over, detecting whether a flatness, a verticality and a compactness of the physical model sample of similar materials are qualified, if the flatness, the verticality and the compactness are qualified, detecting whether the dynamic fiber grating, the ultrasonic probes and the acoustic emission probes on the boundary, pre-embedded in the physical model sample of similar materials work normally or not, if they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in a maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in an intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in a minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of a surrounding rock of a wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of maximum principal stress through the first dynamic hydraulic actuator to induce immediate strain burst, and during a process of applying the disturbance loads, monitoring internal deformation of the physical model sample of similar materials through the dynamic fiber grating, monitoring a wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the second flexible bladder hydraulic pillow to the target value of the intermediate principal stress, unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

9. The large-scale three-dimensional physical simulation test system according to claim 7, wherein, carrying out an immediate strain-structural rock burst simulation test includes the following steps:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover with the high-rigidity three-dimensional reaction frame, and then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;

Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during the printing process, pre-embedding the dynamic fiber grating and the ultrasonic probes at internal set positions in the physical model sample of similar materials, and pre-mounting the acoustic emission probes at set positions on the boundary of the physical model sample of similar materials, at the same time, printing a fault structural plane in the physical model sample of similar materials, wherein a pre-embedded position of the $CO_2$ blast cracking device is near the fault structural plane;

Step IV: performing in-situ normal temperature curing on the printed physical model sample of similar materials, after the curing period is over, detecting whether a flatness, a verticality and a compactness of the physical model sample of similar materials are qualified, if the flatness, the verticality and the compactness are qualified, detecting whether the dynamic fiber grating, the ultrasonic probes and the acoustic emission probes on the boundary, pre-embedded in the physical model sample of similar materials work normally or not, if they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in the maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in the intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in the minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and then continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of the surrounding rock of the wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of the maximum principal stress through the first dynamic hydraulic actuator, and at the same time, starting the $CO_2$ blast cracking device to apply burst impact to the physical model sample of similar materials to induce immediate strain-structural rock burst, and during the process of applying the disturbance loads and the burst impact, monitoring internal deformation of the physical model sample of similar materials through the dynamic fiber grating, monitoring the wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the second flexible bladder hydraulic pillow to the target value of the intermediate principal stress, and then unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

10. The large-scale three-dimensional physical simulation test system according to claim 7, wherein, carrying out a time delayed rock burst simulation test includes the following steps:

Step I: preparing the similar materials, wherein the similar materials comprise the raw materials of water, barite powder, borax, gypsum, cement and a rosin alcohol solution in the ratio of 25% to 20% to 20% to 20% to 10% to 5%;

Step II: disconnecting the frame top cover with the high-rigidity three-dimensional reaction frame, and then moving the drop hammer impact device to a position right above the high-rigidity three-dimensional reaction frame, lifting the frame top cover by the drop hammer impact device, and then moving the drop hammer impact device hanging the frame top cover away from the position right above the high-rigidity three-dimensional reaction frame;

Step III: moving the 3D printer for the physical model sample of similar materials to the position right above the high-rigidity three-dimensional reaction frame, using the prepared similar materials as a printing raw material of the 3D printer for the physical model sample of similar materials, completing in-situ printing of the physical model sample of similar materials in the high-rigidity three-dimensional reaction frame through the 3D printer for the physical model sample of similar materials, and during the printing process, pre-embedding the dynamic fiber grating and the ultrasonic probes at internal set positions in the physical model sample of similar materials, and pre-mounting the acoustic emission probes at set positions on the boundary of the physical model sample of similar materials;

Step IV: performing in-situ normal temperature curing on the printed physical model sample of similar materials, after the curing period is over, detecting whether a flatness, a verticality and a compactness of the physical model sample of similar materials are qualified, if the flatness, the verticality and the compactness are qualified, detecting whether the dynamic fiber grating, the ultrasonic probes and the acoustic emission probes on the boundary, pre-embedded in the physical model sample of similar materials work normally or not, if they work normally, moving the drop hammer impact device hanging the frame top cover to the position right above the high-rigidity three-dimensional reaction frame, and then enabling the frame top cover to drop back to the top of the high-rigidity three-dimensional reaction frame through the drop hammer impact device, and reconnecting the frame top cover with the high-rigidity three-dimensional reaction frame together, and then moving the drop hammer impact device away from the position right above the high-rigidity three-dimensional reaction frame;

Step V: adopting a stress control manner, synchronously controlling the first flexible bladder hydraulic pillow, the second flexible bladder hydraulic pillow and the first dynamic hydraulic actuator to apply prestress to the physical model sample of similar materials to realize target value until prestressed loading in the maximum principal stress direction is completed;

Step VI: adopting the stress control manner, synchronously controlling the third flexible bladder hydraulic pillow and the fourth flexible bladder hydraulic pillow to apply prestress to the physical model sample of similar materials to realize target value until prestressed loading in the intermediate principal stress direction is completed;

Step VII: adopting the stress control manner, synchronously controlling the fifth flexible bladder hydraulic pillow and the second dynamic hydraulic actuator to apply prestress to the physical model sample of similar materials to realize the target value until prestressed loading in the minimum principal stress direction is completed;

Step VIII: adopting the stress control manner, firstly loading the physical model sample of similar materials to the target value of minimum principal stress through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow, and then continuing to load the physical model sample of similar materials to the target value of intermediate principal stress through the first dynamic hydraulic actuator, the first flexible bladder hydraulic pillow, the second flexible bladder hydraulic pillow, the third flexible bladder hydraulic pillow and the fourth flexible bladder hydraulic pillow, and finally, continuing to load the physical model sample of similar materials to the target value of maximum principal stress through the first dynamic hydraulic actuator, the first flexible bladder hydraulic pillow and the second flexible bladder hydraulic pillow;

Step IX: starting the miniature rotary excavation flexible mechanical arm device, controlling the mechanical arm of the miniature rotary excavation flexible mechanical arm device to sequentially penetrate through the simulation excavation hole and the center hole of the fifth flexible bladder hydraulic pillow, and starting excavating on the physical model sample of similar materials in the minimum principal stress direction until the tunnel is formed in the physical model sample of similar materials;

Step X: closing the miniature rotary excavation flexible mechanical arm device, firstly enabling the mechanical arm of the miniature rotary excavation flexible mechanical arm device to exit from the tunnel, the center hole of the fifth flexible bladder hydraulic pillow and the simulation excavation hole, and then sequentially mounting the three-way acceleration sensor and the industrial endoscope in the tunnel, monitoring acceleration data of an elastic wave of the surrounding rock of the wall of the tunnel through the three-way acceleration sensor, and monitoring the damage of the surrounding rock of the wall of the tunnel through the industrial endoscope;

Step XI: performing short-term static stress holding on the physical model sample of similar materials after completing tunnel excavation;

Step XII: after the static stress holding is over, applying disturbance loads based on static pressure of target value of the maximum principal stress through the first dynamic hydraulic actuator to induce low-intensity time delayed rock burst, and then starting the drop hammer impact device, so that the drop hammer rod of the drop hammer impact device freely drops down and impacts the first pressure bearing cushion block, and completing application of external disturbances to induce middle-intensity time delayed rock burst, and finally, starting the split Hopkinson pressure bar device, so that the emission rod of the split Hopkinson pressure bar device impacts the second pressure bearing cushion block to complete further application of the external disturbances to induce high-intensity time delayed rock burst, and during the process of applying the disturbance loads, monitoring internal deformation of the physical model sample of similar materials through the dynamic fiber grating, monitoring the wave velocity of the physical model sample of similar materials in the loading process through the ultrasonic probes, and monitoring acoustic emission signals of the physical model sample of similar materials in the loading process through the acoustic emission probes; and Step XIII: after rock burst occurs, firstly, unloading the loads applied to the physical model sample of similar materials through the first dynamic hydraulic actuator, the first flexible bladder hydraulic pillow and the first flexible bladder hydraulic pillow to the target value of the intermediate principal stress, and then unloading the loads applied to the physical model sample of similar materials through the first dynamic hydraulic actuator, the first flexible bladder hydraulic pillow, the second flexible bladder hydraulic pillow, the third flexible bladder hydraulic pillow and the fourth flexible bladder hydraulic pillow to the target value of the minimum principal stress, and finally, unloading the loads applied to the physical model sample of similar materials through the first dynamic hydraulic actuator, the second dynamic hydraulic actuator, the first flexible bladder hydraulic pillow, the second flexible bladder hydraulic pillow, the third flexible bladder hydraulic pillow, the fourth flexible bladder hydraulic pillow and the fifth flexible bladder hydraulic pillow to 0.

* * * * *